United States Patent
Bruce et al.

(10) Patent No.: US 10,294,448 B1
(45) Date of Patent: May 21, 2019

(54) METHOD FOR DIGESTING ORGANIC MATTER USING A BIODIGESTING APPARATUS COMPRISING AN ANGLED DIGESTION TANK

(71) Applicants: Daniel Bruce, Spokane, WA (US); Margaret Ruhl, Spokane, WA (US)

(72) Inventors: Daniel Bruce, Spokane, WA (US); Margaret Ruhl, Spokane, WA (US)

( * ) Notice: Subject to any disclaimer, the term of this patent is extended or adjusted under 35 U.S.C. 154(b) by 0 days.

(21) Appl. No.: 15/331,500

(22) Filed: Oct. 21, 2016

Related U.S. Application Data

(60) Provisional application No. 62/245,777, filed on Oct. 23, 2015.

(51) Int. Cl.

| | |
|---|---|
| *C12M 1/107* | (2006.01) |
| *C12M 1/00* | (2006.01) |
| *C02F 3/28* | (2006.01) |
| *C02F 11/04* | (2006.01) |
| *C12P 3/00* | (2006.01) |
| *C12P 5/02* | (2006.01) |

(52) U.S. Cl.
CPC .............. *C12M 21/04* (2013.01); *C02F 3/286* (2013.01); *C02F 11/04* (2013.01); *C12M 23/36* (2013.01); *C12M 23/40* (2013.01); *C12M 47/10* (2013.01); *C12P 3/00* (2013.01); *C12P 5/023* (2013.01)

(58) Field of Classification Search
CPC ........ Y02E 50/343; Y02E 50/16; Y02E 50/10; Y02E 50/30; C05F 17/0027; C05F 17/0018; C05F 17/0054; C05F 11/00; C05F 17/00; C10L 2290/26; C10L 2290/06; C10L 2290/542; C10L 3/08; C10L 2290/30; C10L 5/363; C10L 5/445; Y02P 20/145; Y02W 30/43; Y02W 30/47; Y02W 10/37; Y02W 30/20; B09B 3/00; B09B 3/0091; B01D 2251/2062; B01D 53/1462; B01D 53/801; B01D 53/62; C02F 11/04; C02F 2301/106; C02F 2303/02; C02F 2303/26; C02F 3/006; C02F 3/28; C02F 3/2866; C02F 11/02; C02F 2203/002; C02F 2033/006; C02F 2303/12; C02F 3/082; C02F 3/301; C02F 2101/101; C02F 2103/20; C02F 3/2893; C02F 3/30; C02F 2203/00; C02F 3/02; C07C 7/11; C12M 21/04; C12M 47/10; C12M 47/18; C12M 45/04; A61L 11/00; B01J 19/28; B01J 20/22; C10J 2300/0916; C10J 3/72; C12P 2201/00; C12P 2203/00; C12P 7/10; F02B 43/10; Y02T 10/32
See application file for complete search history.

(56) References Cited

U.S. PATENT DOCUMENTS

| | | |
|---|---|---|
| 3,575,791 A | 4/1971 | Messing |
| 3,579,651 A | 5/1971 | Russo |
| 3,824,632 A | 7/1974 | Bach et al. |
| 8,927,265 B2 | 1/2015 | Hansen et al. |
| 2013/0029394 A1* | 1/2013 | Toll .................. A61L 11/00 435/167 |
| 2013/0130346 A1 | 5/2013 | Hansen et al. |

* cited by examiner

*Primary Examiner* — Deborah K Ware
(74) *Attorney, Agent, or Firm* — Wells St. John P.S.

(57) ABSTRACT

Organic matter digesting apparatus and methods are provided that can include a digestion tank operatively coupled to a vertically aligned gas collection tower and methods that can include providing a biodigesting apparatus; inputting organic matter into the biodigesting apparatus; initiating the biodigesting apparatus; and outputting water, methane gas, and solid carbon-based material.

6 Claims, 4 Drawing Sheets

METHOD FOR DIGESTING ORGANIC MATTER USING A BIODIGESTING APPARATUS COMPRISING AN ANGLED DIGESTION TANK

CROSS REFERENCE TO RELATED APPLICATION

This application claims priority to U.S. Provisional Patent Application Ser. No. 62/245,777 which was filed on Oct. 23, 2015, the entirety of which is incorporated by reference herein.

TECHNICAL FIELD

The present disclosure relates generally to a biodigester of organic matter such as sewage, plant material, animal material, and/or other degradable materials. More specifically, the present disclosure provides biodigester assemblies and methods for processing organic matter and separating the processed organic matter.

BACKGROUND

Efficient use of resources has always been an important concept. However, this ideal becomes even more important in light of what society now understands about the dangers of not being conscientious about the environment. This contradicts humanity's reliance on exploiting natural resources. However, there are potential resources that man has not exploited fully as of yet, and some of those opportunities can actually benefit the environment. It is the goal of the present disclosure to provide clean water, usable methane gas, and solid carbon material while disposing of organic matter in an environmentally conscientious manner.

DRAWINGS

Embodiments of the disclosure are described below with reference to the following accompanying drawings.

DESCRIPTION

This disclosure is submitted in furtherance of the constitutional purposes of the U.S. Patent Laws "to promote the progress of science and useful arts" (Article 1, Section 8).

Apparatuses and methods for digesting organic matter are disclosed with reference to FIGS. 1-5. In accordance with example embodiments, materials can be processed with the assemblies and/or methods provided and the processed material products separated. For example, water and/or methane can be products of processed organic matter and these products can be separated from processed organic matter, leaving a solid matter. Example implementations can include removing the water and/or providing same to external water filters and storage. The methane gas can be removed and/or externally processed further and either stored or used; and the remaining solid matter can be removed and/or sent to external cookers.

Figure 1:
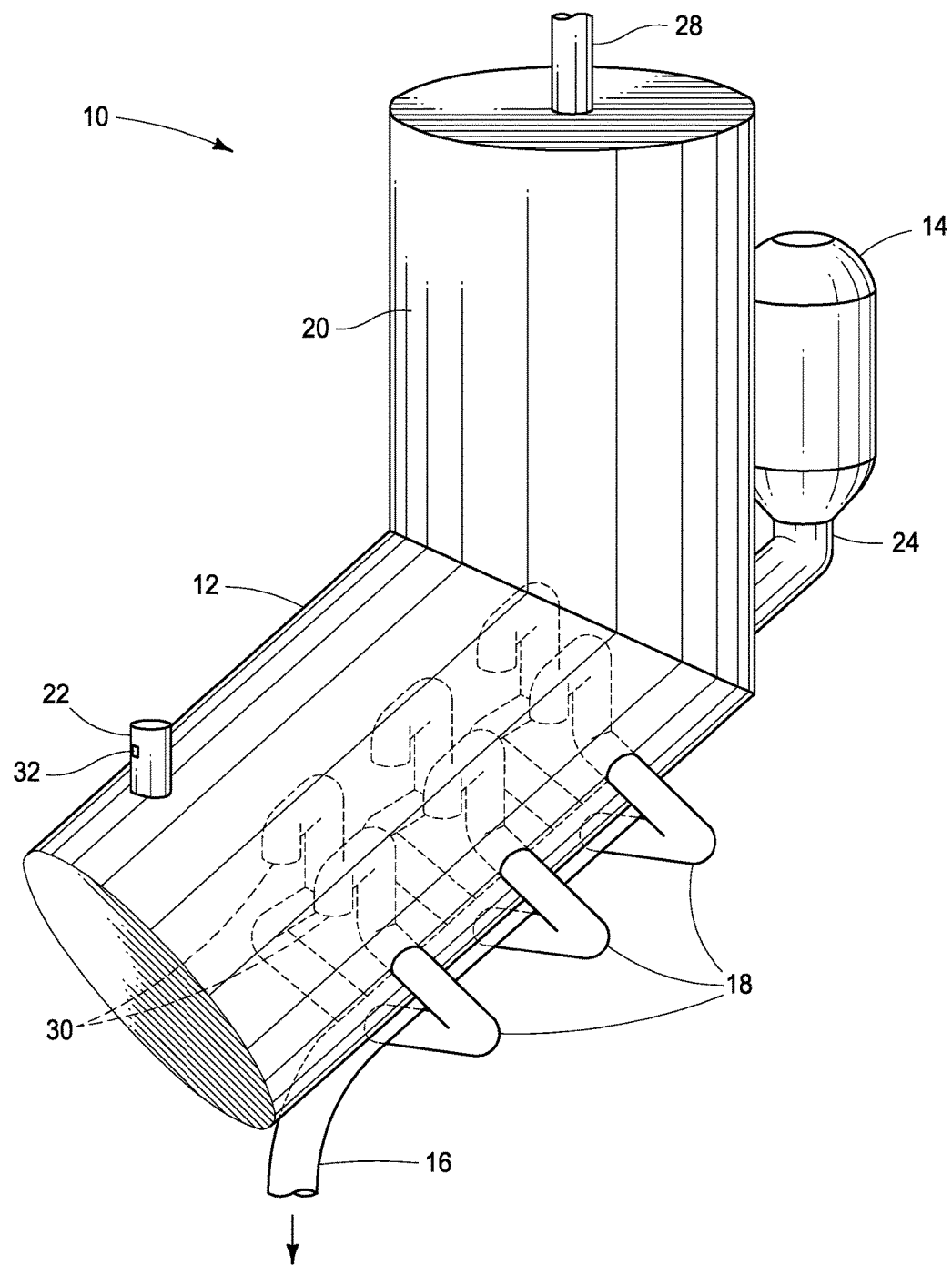
FIG. 1 is a perspective view of a biodigester apparatus according to an embodiment of the disclosure.

Referring first to FIG. 1, a biodigester apparatus 10 is shown. The biodigester combines a digestion tank 12 in fluid communication with a gas collection tower 20. Collection tower 20 can be vertically aligned, such as aligned normal to the ground or floor surface. Digestion tank 12 can extend from the bottom of collection tower 20 at an angle other than normal such as an obtuse angle. A float gauge 22 can be provided in tank 12 and extend vertically up from the lower portion of the digestion tank. Gauge 22 may have indicator 32.

An air slurry separator 14 can be configured to provide feed material into an input conduit 24. As indicated above, the feed material can be sewage, plant material, animal material, and/or degradable materials. Input conduit 24 can be coupled to digestion tank 12. Separator 14 and conduit 24 can be configured to provide feed material to assembly 10 without allowing products to escape assembly 10 through input conduit 24.

Within digestion tank 12 can be provided a manifold of a plurality of conduits 18. These conduits can be configured as multiple pairs as shown and may be configured to receive liquid, such as water product, via intake apertures 30. Conduits 18 can extend to the exterior of tank 12 and then merge into a single liquid output conduit 16.

Gas collection tower 20 can be configured to collect gases that may be generated during processing in digestion tank 12. These gases can be removed from assembly 10 via a gas output conduit 28. As is shown, the fluid communication between tank 12 and tower 20 can be substantially the entire diameter of the tank and/or tower to facilitate the least restrictive generation and transport of gas products. It may be desirable for this fluid connection to be large to restrict the flow of gas products into conduit 24.

Figure 2:
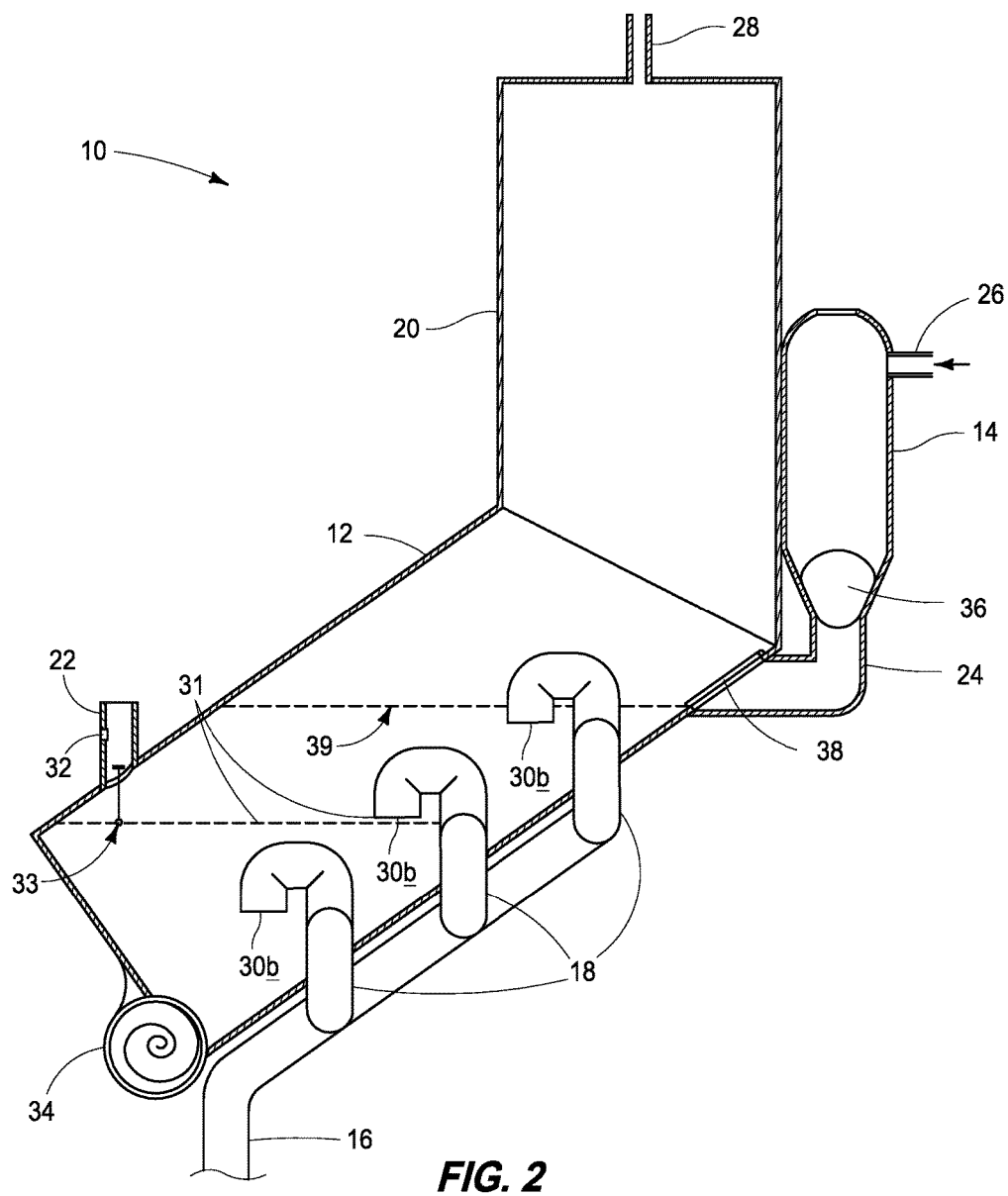
FIG. 2 is a cross sectional view of a biodigester apparatus according to an embodiment of the disclosure.

Referring next to FIG. 2, a cross sectional side view of assembly 10 is shown. As shown, feed material can be input into assembly 10 via an inlet 26 extending into slurry separator 14. Slurry separator 14 includes a float plug assembly 36 that obstructs the entrance of raw organic matter to input conduit 24. At the juncture of the input conduit 24 and the digestion tank 12 is a biased flap gate 38 which serves to maintain a pressure balance, only allowing materials to enter digestion tank 12 when the flap gate 38 opens to form an aperture between input conduit 24 and the digestion tank 12. When the flap gate 38 closes shut after allowing matter to pass into the digestion tank 12, the pressure displacement causes the float plug 36 inside the slurry separator to rise and allow more material into the input conduit 24, where it sits until the pressure causes the flap gate 38 to open again.

Once feed material enters into digestion tank 12, the pressure and temperature within the tank facilitates biodegradation of the matter. This biodegradation can be facilitated bacterially, enzymatically, and/or catalytically, however natural biodegradation is preferred. Gas degradation products rise into gas collection tower 20 and exit out of gas output conduit 28 and on to external gas processing apparatuses not described in this disclosure. From there, the gas is processed and/or stored for immediate utilization.

Water and water vapor biodegradation products can be pulled into the liquid intake apertures 30a, 30b, and 30c respectively, into contributory water conduits 18, and further to the liquid output conduit 16. This water biodegradation product can be sent to external filtration systems not described in this disclosure, and filtered water can be stored or immediately utilized. Solid biodegraded material can travel via gravity into an auger 34, and the material is further broken down in the auger and fed out to external cookers not described in this disclosure where the solid matter can be made into clean, useful charcoal, for example.

With particular emphasis on this view, within the digestion tank 12, as feed material is input into the tank, the matter may fill the tank to above the level of intake aperture 30a and reach a near capacity level 31. When the matter makes contact with float sensor 33, the float gauge indicator 32 on the float gauge 22 will display a signal such as an LED light to indicate that the tank is near a full capacity level 39, and the operator may slow or cease input until enough matter has been digested through the tank 12 through the auger 34. As is shown in this view, the angle of relation of tank 12 and tower 20 facilitates the gravitational migration of feed material through processing and into auger 34.

Figure 3:
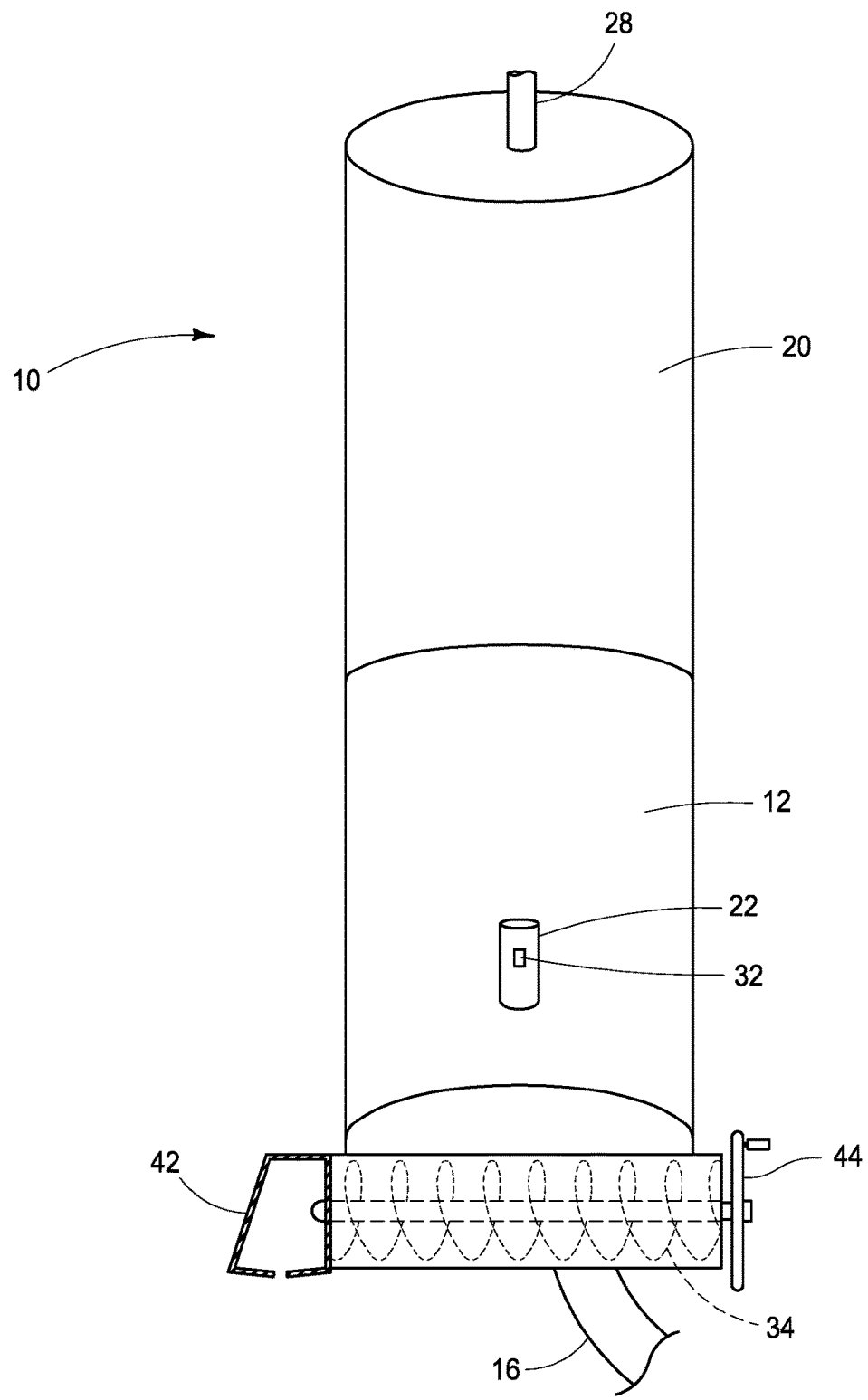
FIG. 3 is a perspective view of the front of a biodigester apparatus according to an embodiment of the disclosure.

Referring next to FIG. 3, a front view of the biodigester apparatus 10 is shown. Auger 34 is shown with a manual crank 44. An operator may also use an automatic crank to initiate the auger. To maintain constant pressure within the tank 12, the output of the auger 34 is a sphincter 42 made from a biased flexible substance such as rubber or other polymer with rubber-like characteristics.

Figure 4:
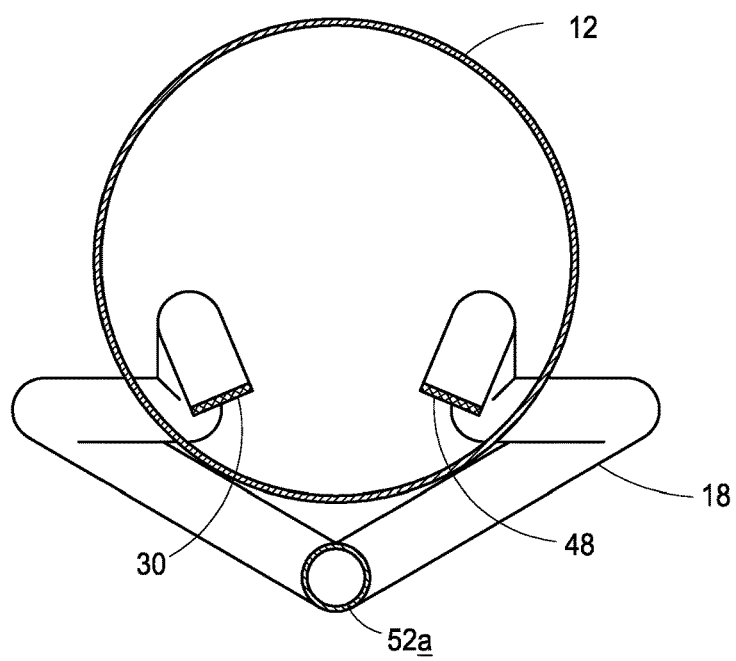
FIG. 4 is a cross sectional view of a digestion chamber of the biodigester apparatus according to an embodiment of the disclosure.

Referring next to FIG. 4, a cross sectional view of inside digestion tank 12 is shown according to one embodiment. In this embodiment, the liquid intake apertures 30 are shown leading to the contributory water conduits 18 respectively. The conduits 18 converge at a juncture 52a. The intake apertures 30 may be capped by filters 48 to keep solid materials from entering the water conduits 18.

Figure 5:
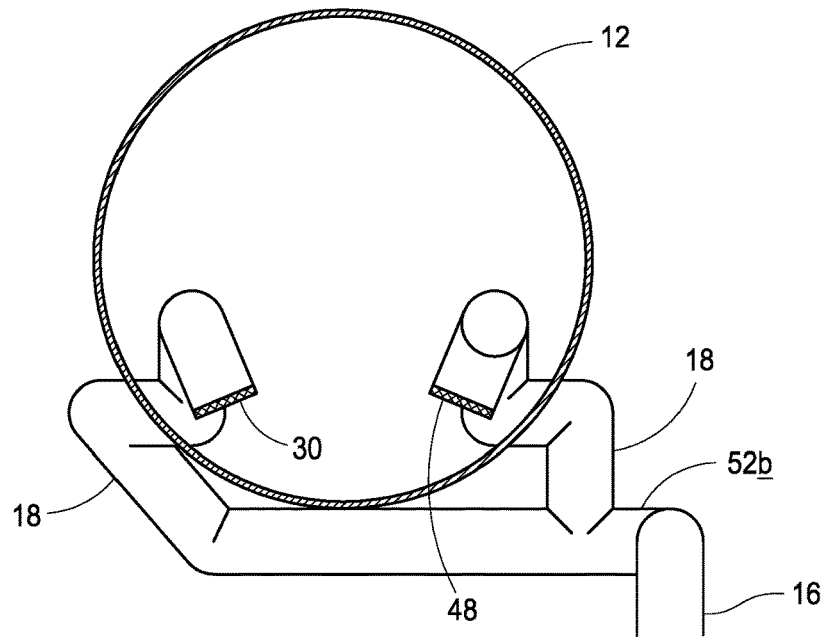
FIG. 5 is a cross sectional view of a digestion chamber of the biodigester apparatus according to an embodiment of the disclosure.

Referring next to FIG. 5, another embodiment is shown as a cross sectional view of inside the digestion tank 12. In this embodiment, the contributory water conduits 18 do not merge directly beneath the tank 12. Instead, the juncture of the conduits 52b is beneath one side of the tank, offset from the conduit closest to the juncture 52b. This embodiment may be preferred to change the suction pressure of the conduits leading to the output conduit 16.

In compliance with the statute, embodiments of the disclosure have been described in language more or less specific as to structural and methodical features. It is to be understood, however, that the entire disclosure is not limited to the specific features and/or embodiments shown and/or described, since the disclosed embodiments comprise forms of putting the disclosure into effect.

The invention claimed is:

1. A method for digesting organic matter comprising:
    providing a biodigesting apparatus comprising a digestion tank in fluid communication with a gas collection tower, the tower extending vertically and directly from an upper portion of the digestion tank, and the digestion tank being aligned at an angle other than normal from the bottom of the tower;
    inputting organic matter into the digestion tank;
    initiating the biodigesting apparatus; and
    outputting water from the digestion tank via a manifold of conduits extending to within the digestion tank, each conduit linearly spaced apart from each other along a sidewall of the digestion tank;
    outputting methane gas via the tower; and
    outputting solid carbon-based material via an auger coupled to the lower end of the digestion tank.

2. The method of claim 1 wherein the inputting of the organic matter further comprises providing the organic matter to the lower portion of the gas collection tower operatively aligned with the digestion tank.

3. The method of claim 2 wherein the organic matter is first air separated prior to entering the digestion tank.

4. The method of claim 1 wherein the inputting of the organic matter further comprises metering the flow of organic matter based on the amount of material in the biodigesting apparatus.

5. The method of claim 1 wherein the water is a by-product of the digestion and is output via a plurality of inverted U-trap configured conduits.

6. The method of claim 1 further comprising compiling the solid carbon-based material via gravity along a lower portion of the angled digestion tank.

* * * * *